(12) United States Patent
Pividori Gurgo et al.

(10) Patent No.: US 10,156,565 B2
(45) Date of Patent: Dec. 18, 2018

(54) PEPTIDE, MAGNETIC PEPTIDE AND METHOD FOR DETECTING CELIAC DISEASE

(71) Applicant: Universitat Autónoma De Barcelona, Barcelona (ES)

(72) Inventors: María I. Pividori Gurgo, Barcelona (ES); Silvina V. Kergaravat, Barcelona (ES)

(73) Assignee: UNIVERSITAT AUTONOMA DE BARCELONA, Barcelona (ES)

( * ) Notice: Subject to any disclaimer, the term of this patent is extended or adjusted under 35 U.S.C. 154(b) by 0 days.

(21) Appl. No.: 15/118,516

(22) PCT Filed: Feb. 16, 2015

(86) PCT No.: PCT/ES2015/070097
§ 371 (c)(1),
(2) Date: Aug. 12, 2016

(87) PCT Pub. No.: WO2015/121526
PCT Pub. Date: Aug. 20, 2015

(65) Prior Publication Data
US 2017/0153233 A1    Jun. 1, 2017

(30) Foreign Application Priority Data
Feb. 14, 2014    (ES) .................................. 201430198

(51) Int. Cl.
*G01N 33/543*    (2006.01)
*G01N 33/564*    (2006.01)
*C07K 14/415*    (2006.01)

(52) U.S. Cl.
CPC ......... *G01N 33/564* (2013.01); *C07K 14/415* (2013.01); *G01N 33/54326* (2013.01); *G01N 2333/415* (2013.01); *G01N 2800/06* (2013.01); *G01N 2800/065* (2013.01)

(58) Field of Classification Search
None
See application file for complete search history.

(56) References Cited

U.S. PATENT DOCUMENTS

| 4,654,267 | A | 3/1987 | Ugelstad et al. | |
| 5,962,641 | A | 10/1999 | Nelson et al. | |
| 2006/0189797 | A1* | 8/2006 | Songe ................ | B01D 15/3828 530/412 |
| 2008/0038760 | A1 | 2/2008 | Mascart et al. | |
| 2009/0311727 | A1 | 12/2009 | Watkins et al. | |
| 2013/0109034 | A1 | 5/2013 | Kumar et al. | |

FOREIGN PATENT DOCUMENTS

| WO | 98/06739 A1 | 2/1998 |
| WO | 00/61647 A1 | 10/2000 |
| WO | 2005/089933 A1 | 9/2005 |
| WO | 2009/131909 A2 | 10/2009 |
| WO | 2013/083866 A1 | 6/2013 |

OTHER PUBLICATIONS

Terpe, "Overview of tag protein fusions: from molecular and biochemical fundamentals to commercial systems", Appl Microbiol Biotechnol, 2003, 523-533.*
Dynal Biotech (Dynabeads® TALON™, pp. 1-2,© 2003; printed Nov. 2003 (Year: 2003).*
Schwertz et al., "Serologic Assay Based on Gliadin-Related Nonapeptides as a Highly Sensitive and Specific Diagnostic Aid in Celiac Disease", Clinical Chemistry; 2004; pp. 2370-2375 (Year: 2004).*
Lindeberg et al. "Immobilized metal ion affinity chromatography (IMAC)", Int. J. Peptide Protein Res., 1991, pp. 253-259 (Year: 1991).*
BD Biosciences BD Biosciences Clontech Protein Purification Products, 2002, p. 1-92 (Year: 2002).*
Aleanzi, M. et al., "Celiac Disease: Antibody Recognition agianst Native and Selectively Deamidated Gliadin Peptides"; Clin. Chem. (2001); vol. 47:11; pp. 2023-2028.
Kergeravat et al., "Magneto immunofluorescence assay for diagnosis of celiac disease"; Anal. Chim Acta., (2013); vol. 798; pp. 89-96.
Laube T. et al. "Magneto immunosensor for gliadin detection in gluten free food-stuff: Towards food safety for celiac patients"; Biosensors and Bioelectronics (2011); vol. 27, pp. 46-52.
Merrifield,R.B. "Solid Phase Peptide Synthesis. I. The Synthesis of a Tetrapeptide"; J.Am.Chem.Soc., (1963), vol. 35, pp. 2149-2154.
Ministry of Health and Consumer Affairs, "Early diagnosis of coeliac disease," Madrid, Spain 2008 (NIPO: 351-08-086-X) 58 pgs. with English Summary attached.
Nomenclature and Symbolism for Amino Acids and Peptides, Pure & Appl. Chem. (1984), vol. 56:5, pp. 595-624, Pergamon Press, LTD. Great Britain.
Sakly, W. et al., "Performance of anti-deamidated gliadin peptides antibodies in celiac disease diagnosis"; Clin. Res. Hepatol. Gastroenterol. (2012); vol. 36; pp. 598-603.
Schwertz E. et al. "Serologic Assay Based on Gliadin- Related Nonapeptides as a Highly Sensitive and Specific Diagnostic Aid in Celiac Disease"; Clinical Chemistry (2004); vol. 50:12; pp. 2370-2375.

(Continued)

*Primary Examiner* — Lianko G Garyu
(74) *Attorney, Agent, or Firm* — Fox Rothschild LLP

(57) ABSTRACT

The present invention relates to a peptide, a magnetic peptide and a method for detecting coeliac disease. It also relates to a deaminated peptide used to prepare said magnetic peptide and to the use of both to detect coeliac disease. Said deaminated peptide comprises a histidine tag and is bonded to a particulated magnetic complex. It also relates to an immunosensor that comprises said magnetic peptide, to an appropriate method for detecting coeliac disease based on a magnetic immunoassay and to a kit that comprises said magnetic peptide.

12 Claims, No Drawings
Specification includes a Sequence Listing.

(56) References Cited

OTHER PUBLICATIONS

Hakansson, et al.: "Crystallization of Peptidase T from *Salmonella typhimurium*", Biological Crystallography, Acta Crystallographica, 2000, vol. D56, pp. 924-926.
Perron-Savard, et al: "Dimerization and DNA Binding of the *Salmonella enterica* PhoP Response Regulator are Phosphorylation Independent", Microbiology, 2005, vol. 151, pp. 3979-3987.
Carson, et al: "His-Tag Impact on Structure", Biological Crystallography, Acta Cryst., 2007, vol. D63, pp. 295-301.

* cited by examiner

SEQUENCE LISTING

```
<160> NUMBER OF SEQ ID NOS: 62

<210> SEQ ID NO 1
<211> LENGTH: 20
<212> TYPE: PRT
<213> ORGANISM: Artificial Sequence
<220> FEATURE:
<223> OTHER INFORMATION: Synthetic peptide
<220> FEATURE:
<221> NAME/KEY: PEPTIDE
<222> LOCATION: (1)..(20)
<223> OTHER INFORMATION: Synthetic peptide X is Q or E, at least one is
      E

<400> SEQUENCE: 1

His His Leu Pro Phe Pro Xaa Xaa Pro Xaa Xaa Pro Phe Pro Xaa Pro
1               5                   10                  15

Xaa Xaa Pro Xaa
            20
```

```
<210> SEQ ID NO 2
<211> LENGTH: 21
<212> TYPE: PRT
<213> ORGANISM: Artificial Sequence
<220> FEATURE:
<223> OTHER INFORMATION: Synthetic peptide
<220> FEATURE:
<221> NAME/KEY: PEPTIDE
<222> LOCATION: (1)..(21)
<223> OTHER INFORMATION: Synthetic peptide X is Q or E, at least one is
      E

<400> SEQUENCE: 2

His His His Leu Pro Phe Pro Xaa Xaa Pro Xaa Xaa Pro Phe Pro Xaa
1               5                   10                  15

Pro Xaa Xaa Pro Xaa
            20

<210> SEQ ID NO 3
<211> LENGTH: 22
<212> TYPE: PRT
<213> ORGANISM: Artificial Sequence
<220> FEATURE:
<223> OTHER INFORMATION: Synthetic peptide
<220> FEATURE:
<221> NAME/KEY: PEPTIDE
<222> LOCATION: (1)..(22)
<223> OTHER INFORMATION: Synthetic peptide X is Q or E, at least one is
      E

<400> SEQUENCE: 3

His His His His Leu Pro Phe Pro Xaa Xaa Pro Xaa Xaa Pro Phe Pro
1               5                   10                  15

Xaa Pro Xaa Xaa Pro Xaa
            20

<210> SEQ ID NO 4
<211> LENGTH: 23
<212> TYPE: PRT
<213> ORGANISM: Artificial Sequence
<220> FEATURE:
<223> OTHER INFORMATION: Synthetic peptide
<220> FEATURE:
<221> NAME/KEY: PEPTIDE
<222> LOCATION: (1)..(23)
<223> OTHER INFORMATION: Synthetic peptide X is Q or E, at least one is
      E

<400> SEQUENCE: 4

His His His His His Leu Pro Phe Pro Xaa Xaa Pro Xaa Xaa Pro Phe
1               5                   10                  15

Pro Xaa Pro Xaa Xaa Pro Xaa
            20

<210> SEQ ID NO 5
<211> LENGTH: 24
<212> TYPE: PRT
<213> ORGANISM: Artificial Sequence
<220> FEATURE:
<223> OTHER INFORMATION: SYNTHETIC PEPTIDE
<220> FEATURE:
<221> NAME/KEY: PEPTIDE
<222> LOCATION: (1)..(24)
<223> OTHER INFORMATION: Synthetic peptide X is Q or E, at least one is
      E

<400> SEQUENCE: 5

His His His His His His Leu Pro Phe Pro Xaa Xaa Pro Xaa Xaa Pro
```

```
                1               5                   10                  15

Phe Pro Xaa Pro Xaa Xaa Pro Xaa
            20

<210> SEQ ID NO 6
<211> LENGTH: 25
<212> TYPE: PRT
<213> ORGANISM: Artificial Sequence
<220> FEATURE:
<223> OTHER INFORMATION: SYNTHETIC PEPTIDE
<220> FEATURE:
<221> NAME/KEY: PEPTIDE
<222> LOCATION: (1)..(25)
<223> OTHER INFORMATION: Synthetic peptide X is Q or E, at least one is
      E

<400> SEQUENCE: 6

His His His His His His His Leu Pro Phe Pro Xaa Xaa Pro Xaa Xaa
1               5                   10                  15

Pro Phe Pro Xaa Pro Xaa Xaa Pro Xaa
            20                  25

<210> SEQ ID NO 7
<211> LENGTH: 26
<212> TYPE: PRT
<213> ORGANISM: Artificial Sequence
<220> FEATURE:
<223> OTHER INFORMATION: SYNTHETIC PEPTIDE
<220> FEATURE:
<221> NAME/KEY: PEPTIDE
<222> LOCATION: (1)..(26)
<223> OTHER INFORMATION: Synthetic peptide X is Q or E, at least one is
      E

<400> SEQUENCE: 7

His His His His His His His His Leu Pro Phe Pro Xaa Xaa Pro Xaa
1               5                   10                  15

Xaa Pro Phe Pro Xaa Pro Xaa Xaa Pro Xaa
            20                  25

<210> SEQ ID NO 8
<211> LENGTH: 27
<212> TYPE: PRT
<213> ORGANISM: Artificial Sequence
<220> FEATURE:
<223> OTHER INFORMATION: SYNTHETIC PEPTIDE
<220> FEATURE:
<221> NAME/KEY: PEPTIDE
<222> LOCATION: (1)..(27)
<223> OTHER INFORMATION: Synthetic peptide X is Q or E, at least one is
      E

<400> SEQUENCE: 8

His His His His His His His His His Leu Pro Phe Pro Xaa Xaa Pro
1               5                   10                  15

Xaa Xaa Pro Phe Pro Xaa Pro Xaa Xaa Pro Xaa
            20                  25

<210> SEQ ID NO 9
<211> LENGTH: 28
<212> TYPE: PRT
<213> ORGANISM: Artificial Sequence
<220> FEATURE:
<223> OTHER INFORMATION: SYNTHETIC PEPTIDE
<220> FEATURE:
<221> NAME/KEY: PEPTIDE
<222> LOCATION: (1)..(28)
<223> OTHER INFORMATION: Synthetic peptide X is Q or E, at least one is
```

E

<400> SEQUENCE: 9

His His His His His His His His His Leu Pro Phe Pro Xaa Xaa
1               5                   10                  15

Pro Xaa Xaa Pro Phe Pro Xaa Pro Xaa Xaa Pro Xaa
            20                  25

<210> SEQ ID NO 10
<211> LENGTH: 29
<212> TYPE: PRT
<213> ORGANISM: Artificial Sequence
<220> FEATURE:
<223> OTHER INFORMATION: SYNTHETIC PEPTIDE
<220> FEATURE:
<221> NAME/KEY: PEPTIDE
<222> LOCATION: (1)..(29)
<223> OTHER INFORMATION: Synthetic peptide X is Q or E, at least one is
      E

<400> SEQUENCE: 10

His His His His His His His His His His Leu Pro Phe Pro Xaa
1               5                   10                  15

Xaa Pro Xaa Xaa Pro Phe Pro Xaa Pro Xaa Xaa Pro Xaa
            20                  25

<210> SEQ ID NO 11
<211> LENGTH: 30
<212> TYPE: PRT
<213> ORGANISM: Artificial Sequence
<220> FEATURE:
<223> OTHER INFORMATION: SYNTHETIC PEPTIDE
<220> FEATURE:
<221> NAME/KEY: PEPTIDE
<222> LOCATION: (1)..(30)
<223> OTHER INFORMATION: Synthetic peptide X is Q or E, at least one is
      E

<400> SEQUENCE: 11

His His His His His His His His His His His Leu Pro Phe Pro
1               5                   10                  15

Xaa Xaa Pro Xaa Xaa Pro Phe Pro Xaa Pro Xaa Xaa Pro Xaa
            20                  25                  30

<210> SEQ ID NO 12
<211> LENGTH: 31
<212> TYPE: PRT
<213> ORGANISM: Artificial Sequence
<220> FEATURE:
<223> OTHER INFORMATION: SYNTHETIC PEPTIDE
<220> FEATURE:
<221> NAME/KEY: PEPTIDE
<222> LOCATION: (1)..(31)
<223> OTHER INFORMATION: Synthetic peptide X is Q or E, at least one is
      E

<400> SEQUENCE: 12

His His His His His His His His His His His His Leu Pro Phe
1               5                   10                  15

Pro Xaa Xaa Pro Xaa Xaa Pro Phe Pro Xaa Pro Xaa Xaa Pro Xaa
            20                  25                  30

<210> SEQ ID NO 13
<211> LENGTH: 32
<212> TYPE: PRT
<213> ORGANISM: Artificial Sequence
<220> FEATURE:

<223> OTHER INFORMATION: SYNTHETIC PEPTIDE
<220> FEATURE:
<221> NAME/KEY: PEPTIDE
<222> LOCATION: (1)..(32)
<223> OTHER INFORMATION: Synthetic peptide X is Q or E, at least one is
      E

<400> SEQUENCE: 13

His His His His His His His His His His His His His His Leu Pro
1               5                   10                  15

Phe Pro Xaa Xaa Pro Xaa Xaa Pro Phe Pro Xaa Pro Xaa Xaa Pro Xaa
            20                  25                  30

<210> SEQ ID NO 14
<211> LENGTH: 33
<212> TYPE: PRT
<213> ORGANISM: Artificial Sequence
<220> FEATURE:
<223> OTHER INFORMATION: SYNTHETIC PEPTIDE
<220> FEATURE:
<221> NAME/KEY: PEPTIDE
<222> LOCATION: (1)..(33)
<223> OTHER INFORMATION: Synthetic peptide X is Q or E, at least one is
      E

<400> SEQUENCE: 14

His His His His His His His His His His His His His His His Leu
1               5                   10                  15

Pro Phe Pro Xaa Xaa Pro Xaa Xaa Pro Phe Pro Xaa Pro Xaa Xaa Pro
            20                  25                  30

Xaa

<210> SEQ ID NO 15
<211> LENGTH: 34
<212> TYPE: PRT
<213> ORGANISM: Artificial Sequence
<220> FEATURE:
<223> OTHER INFORMATION: SYNTHETIC PEPTIDE
<220> FEATURE:
<221> NAME/KEY: PEPTIDE
<222> LOCATION: (1)..(34)
<223> OTHER INFORMATION: Synthetic peptide X is Q or E, at least one is
      E

<400> SEQUENCE: 15

His His His His His His His His His His His His His His His His
1               5                   10                  15

Leu Pro Phe Pro Xaa Xaa Pro Xaa Xaa Pro Phe Pro Xaa Pro Xaa Xaa
            20                  25                  30

Pro Xaa

<210> SEQ ID NO 16
<211> LENGTH: 35
<212> TYPE: PRT
<213> ORGANISM: Artificial Sequence
<220> FEATURE:
<223> OTHER INFORMATION: SYNTHETIC PEPTIDE
<220> FEATURE:
<221> NAME/KEY: PEPTIDE
<222> LOCATION: (1)..(35)
<223> OTHER INFORMATION: Synthetic peptide X is Q or E, at least one is
      E

<400> SEQUENCE: 16

His His His His His His His His His His His His His His His His
1               5                   10                  15

His Leu Pro Phe Pro Xaa Xaa Pro Xaa Xaa Pro Phe Pro Xaa Pro Xaa
                20                  25                  30

Xaa Pro Xaa
        35

<210> SEQ ID NO 17
<211> LENGTH: 36
<212> TYPE: PRT
<213> ORGANISM: Artificial Sequence
<220> FEATURE:
<223> OTHER INFORMATION: SYNTHETIC PEPTIDE
<220> FEATURE:
<221> NAME/KEY: PEPTIDE
<222> LOCATION: (1)..(36)
<223> OTHER INFORMATION: Synthetic peptide X is Q or E, at least one is
      E

<400> SEQUENCE: 17

His His His His His His His His His His His His His His His
1               5                   10                  15

His His Leu Pro Phe Pro Xaa Xaa Pro Xaa Xaa Pro Phe Pro Xaa Pro
                20                  25                  30

Xaa Xaa Pro Xaa
        35

<210> SEQ ID NO 18
<211> LENGTH: 37
<212> TYPE: PRT
<213> ORGANISM: Artificial Sequence
<220> FEATURE:
<223> OTHER INFORMATION: SYNTHETIC PEPTIDE
<220> FEATURE:
<221> NAME/KEY: PEPTIDE
<222> LOCATION: (1)..(37)
<223> OTHER INFORMATION: Synthetic peptide X is Q or E, at least one is
      E

<400> SEQUENCE: 18

His His His His His His His His His His His His His His His His
1               5                   10                  15

His His His Leu Pro Phe Pro Xaa Xaa Pro Xaa Xaa Pro Phe Pro Xaa
                20                  25                  30

Pro Xaa Xaa Pro Xaa
        35

<210> SEQ ID NO 19
<211> LENGTH: 38
<212> TYPE: PRT
<213> ORGANISM: Artificial Sequence
<220> FEATURE:
<223> OTHER INFORMATION: SYNTHETIC PEPTIDE
<220> FEATURE:
<221> NAME/KEY: PEPTIDE
<222> LOCATION: (1)..(38)
<223> OTHER INFORMATION: Synthetic peptide X is Q or E, at least one is
      E

<400> SEQUENCE: 19

His His His His His His His His His His His His His His His His
1               5                   10                  15

His His His His Leu Pro Phe Pro Xaa Xaa Pro Xaa Xaa Pro Phe Pro
                20                  25                  30

Xaa Pro Xaa Xaa Pro Xaa
        35

```
<210> SEQ ID NO 20
<211> LENGTH: 20
<212> TYPE: PRT
<213> ORGANISM: Artificial Sequence
<220> FEATURE:
<223> OTHER INFORMATION: SYNTHETIC PEPTIDE
<220> FEATURE:
<221> NAME/KEY: PEPTIDE
<222> LOCATION: (1)..(20)
<223> OTHER INFORMATION: Synthetic peptide X is Q or E, at least one is
      E

<400> SEQUENCE: 20

Leu Pro Phe Pro Xaa Xaa Pro Xaa Xaa Pro Phe Pro Xaa Pro Xaa Xaa
1               5                   10                  15

Pro Xaa His His
            20

<210> SEQ ID NO 21
<211> LENGTH: 21
<212> TYPE: PRT
<213> ORGANISM: Artificial Sequence
<220> FEATURE:
<223> OTHER INFORMATION: SYNTHETIC PEPTIDE
<220> FEATURE:
<221> NAME/KEY: PEPTIDE
<222> LOCATION: (1)..(21)
<223> OTHER INFORMATION: Synthetic peptide X is Q or E, at least one is
      E

<400> SEQUENCE: 21

Leu Pro Phe Pro Xaa Xaa Pro Xaa Xaa Pro Phe Pro Xaa Pro Xaa Xaa
1               5                   10                  15

Pro Xaa His His His
            20

<210> SEQ ID NO 22
<211> LENGTH: 22
<212> TYPE: PRT
<213> ORGANISM: Artificial Sequence
<220> FEATURE:
<223> OTHER INFORMATION: SYNTHETIC PEPTIDE
<220> FEATURE:
<221> NAME/KEY: PEPTIDE
<222> LOCATION: (1)..(22)
<223> OTHER INFORMATION: Synthetic peptide X is Q or E, at least one is
      E

<400> SEQUENCE: 22

Leu Pro Phe Pro Xaa Xaa Pro Xaa Xaa Pro Phe Pro Xaa Pro Xaa Xaa
1               5                   10                  15

Pro Xaa His His His His
            20

<210> SEQ ID NO 23
<211> LENGTH: 23
<212> TYPE: PRT
<213> ORGANISM: Artificial Sequence
<220> FEATURE:
<223> OTHER INFORMATION: SYNTHETIC PEPTIDE
<220> FEATURE:
<221> NAME/KEY: PEPTIDE
<222> LOCATION: (1)..(23)
<223> OTHER INFORMATION: Synthetic peptide X is Q or E, at least one is
      E

<400> SEQUENCE: 23

Leu Pro Phe Pro Xaa Xaa Pro Xaa Xaa Pro Phe Pro Xaa Pro Xaa Xaa
1               5                   10                  15
```

Pro Xaa His His His His His
            20

<210> SEQ ID NO 24
<211> LENGTH: 24
<212> TYPE: PRT
<213> ORGANISM: Artificial Sequence
<220> FEATURE:
<223> OTHER INFORMATION: SYNTHETIC PEPTIDE
<220> FEATURE:
<221> NAME/KEY: PEPTIDE
<222> LOCATION: (1)..(24)
<223> OTHER INFORMATION: Synthetic peptide X is Q or E, at least one is
      E

<400> SEQUENCE: 24

Leu Pro Phe Pro Xaa Xaa Pro Xaa Xaa Pro Phe Pro Xaa Pro Xaa Xaa
1               5                   10                  15

Pro Xaa His His His His His His
            20

<210> SEQ ID NO 25
<211> LENGTH: 25
<212> TYPE: PRT
<213> ORGANISM: Artificial Sequence
<220> FEATURE:
<223> OTHER INFORMATION: SYNTHETIC PEPTIDE
<220> FEATURE:
<221> NAME/KEY: PEPTIDE
<222> LOCATION: (1)..(25)
<223> OTHER INFORMATION: Synthetic peptide X is Q or E, at least one is
      E

<400> SEQUENCE: 25

Leu Pro Phe Pro Xaa Xaa Pro Xaa Xaa Pro Phe Pro Xaa Pro Xaa Xaa
1               5                   10                  15

Pro Xaa His His His His His His His
            20                  25

<210> SEQ ID NO 26
<211> LENGTH: 26
<212> TYPE: PRT
<213> ORGANISM: Artificial Sequence
<220> FEATURE:
<223> OTHER INFORMATION: SYNTHETIC PEPTIDE
<220> FEATURE:
<221> NAME/KEY: PEPTIDE
<222> LOCATION: (1)..(26)
<223> OTHER INFORMATION: Synthetic peptide X is Q or E, at least one is
      E

<400> SEQUENCE: 26

Leu Pro Phe Pro Xaa Xaa Pro Xaa Xaa Pro Phe Pro Xaa Pro Xaa Xaa
1               5                   10                  15

Pro Xaa His His His His His His His His
            20                  25

<210> SEQ ID NO 27
<211> LENGTH: 27
<212> TYPE: PRT
<213> ORGANISM: Artificial Sequence
<220> FEATURE:
<223> OTHER INFORMATION: SYNTHETIC PEPTIDE
<220> FEATURE:
<221> NAME/KEY: PEPTIDE
<222> LOCATION: (1)..(27)
<223> OTHER INFORMATION: Synthetic peptide X is Q or E, at least one is
      E -continued

```
<400> SEQUENCE: 27

Leu Pro Phe Pro Xaa Xaa Pro Xaa Xaa Pro Phe Pro Xaa Pro Xaa Xaa
1               5                   10                  15

Pro Xaa His His His His His His His His
            20                  25

<210> SEQ ID NO 28
<211> LENGTH: 28
<212> TYPE: PRT
<213> ORGANISM: Artificial Sequence
<220> FEATURE:
<223> OTHER INFORMATION: SYNTHETIC PEPTIDE
<220> FEATURE:
<221> NAME/KEY: PEPTIDE
<222> LOCATION: (1)..(28)
<223> OTHER INFORMATION: Synthetic peptide X is Q or E, at least one is
      E

<400> SEQUENCE: 28

Leu Pro Phe Pro Xaa Xaa Pro Xaa Xaa Pro Phe Pro Xaa Pro Xaa Xaa
1               5                   10                  15

Pro Xaa His His His His His His His His His
            20                  25

<210> SEQ ID NO 29
<211> LENGTH: 29
<212> TYPE: PRT
<213> ORGANISM: Artificial Sequence
<220> FEATURE:
<223> OTHER INFORMATION: SYNTHETIC PEPTIDE
<220> FEATURE:
<221> NAME/KEY: PEPTIDE
<222> LOCATION: (1)..(29)
<223> OTHER INFORMATION: Synthetic peptide X is Q or E, at least one is
      E

<400> SEQUENCE: 29

Leu Pro Phe Pro Xaa Xaa Pro Xaa Xaa Pro Phe Pro Xaa Pro Xaa Xaa
1               5                   10                  15

Pro Xaa His His His His His His His His His His
            20                  25

<210> SEQ ID NO 30
<211> LENGTH: 30
<212> TYPE: PRT
<213> ORGANISM: Artificial Sequence
<220> FEATURE:
<223> OTHER INFORMATION: SYNTHETIC PEPTIDE
<220> FEATURE:
<221> NAME/KEY: PEPTIDE
<222> LOCATION: (1)..(30)
<223> OTHER INFORMATION: Synthetic peptide X is Q or E, at least one is
      E

<400> SEQUENCE: 30

Leu Pro Phe Pro Xaa Xaa Pro Xaa Xaa Pro Phe Pro Xaa Pro Xaa Xaa
1               5                   10                  15

Pro Xaa His His His His His His His His His His His
            20                  25                  30

<210> SEQ ID NO 31
<211> LENGTH: 31
<212> TYPE: PRT
<213> ORGANISM: Artificial Sequence
<220> FEATURE:
<223> OTHER INFORMATION: SYNTHETIC PEPTIDE
```

```
<220> FEATURE:
<221> NAME/KEY: PEPTIDE
<222> LOCATION: (1)..(31)
<223> OTHER INFORMATION: Synthetic peptide X is Q or E, at least one is
      E

<400> SEQUENCE: 31

Leu Pro Phe Pro Xaa Xaa Pro Xaa Xaa Pro Phe Pro Xaa Pro Xaa Xaa
1               5                   10                  15

Pro Xaa His His His His His His His His His His His His His
            20                  25                  30

<210> SEQ ID NO 32
<211> LENGTH: 32
<212> TYPE: PRT
<213> ORGANISM: Artificial Sequence
<220> FEATURE:
<223> OTHER INFORMATION: SYNTHETIC PEPTIDE
<220> FEATURE:
<221> NAME/KEY: PEPTIDE
<222> LOCATION: (1)..(32)
<223> OTHER INFORMATION: Synthetic peptide X is Q or E, at least one is
      E

<400> SEQUENCE: 32

Leu Pro Phe Pro Xaa Xaa Pro Xaa Xaa Pro Phe Pro Xaa Pro Xaa Xaa
1               5                   10                  15

Pro Xaa His His His His His His His His His His His His His
            20                  25                  30

<210> SEQ ID NO 33
<211> LENGTH: 33
<212> TYPE: PRT
<213> ORGANISM: Artificial Sequence
<220> FEATURE:
<223> OTHER INFORMATION: SYNTHETIC PEPTIDE
<220> FEATURE:
<221> NAME/KEY: PEPTIDE
<222> LOCATION: (1)..(33)
<223> OTHER INFORMATION: Synthetic peptide X is Q or E, at least one is
      E

<400> SEQUENCE: 33

Leu Pro Phe Pro Xaa Xaa Pro Xaa Xaa Pro Phe Pro Xaa Pro Xaa Xaa
1               5                   10                  15

Pro Xaa His His His His His His His His His His His His His
            20                  25                  30

His

<210> SEQ ID NO 34
<211> LENGTH: 34
<212> TYPE: PRT
<213> ORGANISM: Artificial Sequence
<220> FEATURE:
<223> OTHER INFORMATION: SYNTHETIC PEPTIDE
<220> FEATURE:
<221> NAME/KEY: PEPTIDE
<222> LOCATION: (1)..(34)
<223> OTHER INFORMATION: Synthetic peptide X is Q or E, at least one is
      E

<400> SEQUENCE: 34

Leu Pro Phe Pro Xaa Xaa Pro Xaa Xaa Pro Phe Pro Xaa Pro Xaa Xaa
1               5                   10                  15

Pro Xaa His His His His His His His His His His His His His His
            20                  25                  30
```

His His

<210> SEQ ID NO 35
<211> LENGTH: 35
<212> TYPE: PRT
<213> ORGANISM: Artificial Sequence
<220> FEATURE:
<223> OTHER INFORMATION: SYNTHETIC PEPTIDE
<220> FEATURE:
<221> NAME/KEY: PEPTIDE
<222> LOCATION: (1)..(35)
<223> OTHER INFORMATION: Synthetic peptide X is Q or E, at least one is
      E

<400> SEQUENCE: 35

Leu Pro Phe Pro Xaa Xaa Pro Xaa Xaa Pro Phe Pro Xaa Pro Xaa Xaa
1               5                   10                  15

Pro Xaa His His His His His His His His His His His His His
            20                  25                  30

His His His
        35

<210> SEQ ID NO 36
<211> LENGTH: 36
<212> TYPE: PRT
<213> ORGANISM: Artificial Sequence
<220> FEATURE:
<223> OTHER INFORMATION: SYNTHETIC PEPTIDE
<220> FEATURE:
<221> NAME/KEY: PEPTIDE
<222> LOCATION: (1)..(36)
<223> OTHER INFORMATION: Synthetic peptide X is Q or E, at least one is
      E

<400> SEQUENCE: 36

Leu Pro Phe Pro Xaa Xaa Pro Xaa Xaa Pro Phe Pro Xaa Pro Xaa Xaa
1               5                   10                  15

Pro Xaa His His His His His His His His His His His His His
            20                  25                  30

His His His His
        35

<210> SEQ ID NO 37
<211> LENGTH: 37
<212> TYPE: PRT
<213> ORGANISM: Artificial Sequence
<220> FEATURE:
<223> OTHER INFORMATION: SYNTHETIC PEPTIDE
<220> FEATURE:
<221> NAME/KEY: PEPTIDE
<222> LOCATION: (1)..(37)
<223> OTHER INFORMATION: Synthetic peptide X is Q or E, at least one is
      E

<400> SEQUENCE: 37

Leu Pro Phe Pro Xaa Xaa Pro Xaa Xaa Pro Phe Pro Xaa Pro Xaa Xaa
1               5                   10                  15

Pro Xaa His His His His His His His His His His His His His
            20                  25                  30

His His His His His
        35

<210> SEQ ID NO 38
<211> LENGTH: 38
<212> TYPE: PRT
<213> ORGANISM: Artificial Sequence

```
<220> FEATURE:
<223> OTHER INFORMATION: SYNTHETIC PEPTIDE
<220> FEATURE:
<221> NAME/KEY: PEPTIDE
<222> LOCATION: (1)..(38)
<223> OTHER INFORMATION: Synthetic peptide X is Q or E, at least one is
      E

<400> SEQUENCE: 38

Leu Pro Phe Pro Xaa Xaa Pro Xaa Xaa Pro Phe Pro Xaa Pro Xaa Xaa
1               5                   10                  15

Pro Xaa His His His His His His His His His His His His His
            20                  25                  30

His His His His His His
            35

<210> SEQ ID NO 39
<211> LENGTH: 24
<212> TYPE: PRT
<213> ORGANISM: Artificial Sequence
<220> FEATURE:
<223> OTHER INFORMATION: SYNTHETIC PEPTIDE

<400> SEQUENCE: 39

His His His His His His Leu Pro Phe Pro Glu Gln Pro Glu Gln Pro
1               5                   10                  15

Phe Pro Gln Pro Glu Gln Pro Gln
            20

<210> SEQ ID NO 40
<211> LENGTH: 18
<212> TYPE: PRT
<213> ORGANISM: Artificial Sequence
<220> FEATURE:
<223> OTHER INFORMATION: SYNTHETIC PEPTIDE

<400> SEQUENCE: 40

Leu Pro Phe Pro Glu Gln Pro Glu Gln Pro Phe Pro Gln Pro Glu Gln
1               5                   10                  15

Pro Gln

<210> SEQ ID NO 41
<211> LENGTH: 18
<212> TYPE: PRT
<213> ORGANISM: Artificial Sequence
<220> FEATURE:
<223> OTHER INFORMATION: SYNTHETIC PEPTIDE

<400> SEQUENCE: 41

Leu Pro Phe Pro Gln Gln Pro Glu Gln Pro Phe Pro Gln Pro Glu Gln
1               5                   10                  15

Pro Gln

<210> SEQ ID NO 42
<211> LENGTH: 18
<212> TYPE: PRT
<213> ORGANISM: Artificial Sequence
<220> FEATURE:
<223> OTHER INFORMATION: SYNTHETIC PEPTIDE

<400> SEQUENCE: 42

Leu Pro Phe Pro Glu Gln Pro Gln Gln Pro Phe Pro Gln Pro Glu Gln
1               5                   10                  15

Pro Gln
```

<210> SEQ ID NO 43
<211> LENGTH: 18
<212> TYPE: PRT
<213> ORGANISM: Artificial Sequence
<220> FEATURE:
<223> OTHER INFORMATION: SYNTHETIC PEPTIDE

<400> SEQUENCE: 43

Leu Pro Phe Pro Glu Gln Pro Glu Gln Pro Phe Pro Gln Pro Gln Gln
1               5                   10                  15

Pro Gln

<210> SEQ ID NO 44
<211> LENGTH: 18
<212> TYPE: PRT
<213> ORGANISM: Artificial Sequence
<220> FEATURE:
<223> OTHER INFORMATION: SYNTHETIC PEPTIDE

<400> SEQUENCE: 44

Leu Pro Phe Pro Gln Gln Pro Gln Gln Pro Phe Pro Gln Pro Gln Gln
1               5                   10                  15

Pro Glu

<210> SEQ ID NO 45
<211> LENGTH: 18
<212> TYPE: PRT
<213> ORGANISM: Artificial Sequence
<220> FEATURE:
<223> OTHER INFORMATION: SYNTHETIC PEPTIDE

<400> SEQUENCE: 45

Leu Pro Phe Pro Gln Gln Pro Gln Gln Pro Phe Pro Gln Pro Gln Glu
1               5                   10                  15

Pro Gln

<210> SEQ ID NO 46
<211> LENGTH: 18
<212> TYPE: PRT
<213> ORGANISM: Artificial Sequence
<220> FEATURE:
<223> OTHER INFORMATION: SYNTHETIC PEPTIDE

<400> SEQUENCE: 46

Leu Pro Phe Pro Gln Gln Pro Gln Gln Pro Phe Pro Gln Pro Glu Gln
1               5                   10                  15

Pro Gln

<210> SEQ ID NO 47
<211> LENGTH: 18
<212> TYPE: PRT
<213> ORGANISM: Artificial Sequence
<220> FEATURE:
<223> OTHER INFORMATION: SYNTHETIC PEPTIDE

<400> SEQUENCE: 47

Leu Pro Phe Pro Gln Gln Pro Gln Gln Pro Phe Pro Glu Pro Gln Gln
1               5                   10                  15

Pro Gln

<210> SEQ ID NO 48
<211> LENGTH: 18

-continued

<212> TYPE: PRT
<213> ORGANISM: Artificial Sequence
<220> FEATURE:
<223> OTHER INFORMATION: SYNTHETIC PEPTIDE

<400> SEQUENCE: 48

Leu Pro Phe Pro Gln Gln Pro Gln Glu Pro Phe Pro Gln Pro Gln Gln
1               5                   10                  15

Pro Gln

<210> SEQ ID NO 49
<211> LENGTH: 18
<212> TYPE: PRT
<213> ORGANISM: Artificial Sequence
<220> FEATURE:
<223> OTHER INFORMATION: SYNTHETIC PEPTIDE

<400> SEQUENCE: 49

Leu Pro Phe Pro Gln Gln Pro Glu Gln Pro Phe Pro Gln Pro Gln Gln
1               5                   10                  15

Pro Gln

<210> SEQ ID NO 50
<211> LENGTH: 18
<212> TYPE: PRT
<213> ORGANISM: Artificial Sequence
<220> FEATURE:
<223> OTHER INFORMATION: SYNTHETIC PEPTIDE

<400> SEQUENCE: 50

Leu Pro Phe Pro Gln Glu Pro Gln Gln Pro Phe Pro Gln Pro Gln Gln
1               5                   10                  15

Pro Gln

<210> SEQ ID NO 51
<211> LENGTH: 18
<212> TYPE: PRT
<213> ORGANISM: Artificial Sequence
<220> FEATURE:
<223> OTHER INFORMATION: SYNTHETIC PEPTIDE

<400> SEQUENCE: 51

Leu Pro Phe Pro Glu Gln Pro Gln Gln Pro Phe Pro Gln Pro Gln Gln
1               5                   10                  15

Pro Gln

<210> SEQ ID NO 52
<211> LENGTH: 19
<212> TYPE: PRT
<213> ORGANISM: Artificial Sequence
<220> FEATURE:
<223> OTHER INFORMATION: SYNTHETIC PEPTIDE

<400> SEQUENCE: 52

Leu Pro Phe Pro Glu Gln Pro Glu Gln Pro Phe Pro Gln Pro Glu Gln
1               5                   10                  15

Pro Gln Lys

<210> SEQ ID NO 53
<211> LENGTH: 24
<212> TYPE: PRT
<213> ORGANISM: Artificial sequence
<220> FEATURE:
<223> OTHER INFORMATION: Synthetic peptide

<400> SEQUENCE: 53

His His His His His His Leu Pro Phe Pro Gln Gln Pro Gln Gln Pro
1               5                   10                  15

Phe Pro Gln Pro Gln Gln Pro Gln
            20

<210> SEQ ID NO 54
<211> LENGTH: 24
<212> TYPE: PRT
<213> ORGANISM: Artificial sequence
<220> FEATURE:
<223> OTHER INFORMATION: Synthetic peptide

<400> SEQUENCE: 54

Leu Pro Phe Pro Glu Gln Pro Glu Gln Pro Phe Pro Gln Pro Glu Gln
1               5                   10                  15

Pro Gln His His His His His His
            20

<210> SEQ ID NO 55
<211> LENGTH: 24
<212> TYPE: PRT
<213> ORGANISM: Artificial sequence
<220> FEATURE:
<223> OTHER INFORMATION: Synthetic peptide

<400> SEQUENCE: 55

Leu Pro Phe Pro Glu Gln Pro Glu Gln Pro Phe Pro Gln Pro Glu Glu
1               5                   10                  15

Pro Gln His His His His His His
            20

<210> SEQ ID NO 56
<211> LENGTH: 20
<212> TYPE: PRT
<213> ORGANISM: Artificial sequence
<220> FEATURE:
<223> OTHER INFORMATION: Synthetic peptide

<400> SEQUENCE: 56

Leu Pro Phe Pro Glu Gln Pro Glu Gln Pro Phe Pro Gln Pro Glu Gln
1               5                   10                  15

Pro Gln His His
            20

<210> SEQ ID NO 57
<211> LENGTH: 22
<212> TYPE: PRT
<213> ORGANISM: Artificial sequence
<220> FEATURE:
<223> OTHER INFORMATION: Synthetic peptide

<400> SEQUENCE: 57

His His His His Leu Pro Phe Pro Glu Gln Pro Glu Gln Pro Phe Pro
1               5                   10                  15

Gln Pro Glu Gln Pro Gln
            20

<210> SEQ ID NO 58
<211> LENGTH: 28
<212> TYPE: PRT
<213> ORGANISM: Artificial sequence
<220> FEATURE:

<223> OTHER INFORMATION: Synthetic peptide

<400> SEQUENCE: 58

His His His His His His His His Leu Pro Phe Pro Glu Gln
1               5                   10                  15

Pro Glu Gln Pro Phe Pro Gln Pro Glu Gln Pro Gln
            20                  25

<210> SEQ ID NO 59
<211> LENGTH: 24
<212> TYPE: PRT
<213> ORGANISM: Artificial sequence
<220> FEATURE:
<223> OTHER INFORMATION: Synthetic peptide

<400> SEQUENCE: 59

Leu Pro Phe Pro Glu Gln Pro Glu Gln Pro Phe Pro Gln Pro Glu Gln
1               5                   10                  15

Pro Gln His His His His His His
            20

<210> SEQ ID NO 60
<211> LENGTH: 24
<212> TYPE: PRT
<213> ORGANISM: Artificial sequence
<220> FEATURE:
<223> OTHER INFORMATION: Synthetic peptide

<400> SEQUENCE: 60

Leu Pro Phe Pro Glu Gln Pro Glu Gln Pro Phe Pro Glu Pro Glu Gln
1               5                   10                  15

Pro Gln His His His His His His
            20

<210> SEQ ID NO 61
<211> LENGTH: 20
<212> TYPE: PRT
<213> ORGANISM: Artificial sequence
<220> FEATURE:
<223> OTHER INFORMATION: Synthetic peptide

<400> SEQUENCE: 61

His His Leu Pro Phe Pro Glu Gln Pro Glu Gln Pro Phe Pro Gln Pro
1               5                   10                  15

Glu Gln Pro Gln
            20

<210> SEQ ID NO 62
<211> LENGTH: 20
<212> TYPE: PRT
<213> ORGANISM: Artificial Sequence
<220> FEATURE:
<223> OTHER INFORMATION: Synthetic peptide
<220> FEATURE:
<221> NAME/KEY: PEPTIDE
<222> LOCATION: (1)..(20)
<223> OTHER INFORMATION: Synthetic peptide X is Q or E, at least one is
      E
<220> FEATURE:
<221> NAME/KEY: PEPTIDE
<222> LOCATION: (1)..(20)
<223> OTHER INFORMATION: The N-terminal is (His)n;
      the C-terminal is (His)m;
      n is comprised between 2 and 20, and m is 0, or
      m is comprised between 2 and 20, and n is 0

<400> SEQUENCE: 62

```
His Leu Pro Phe Pro Xaa Xaa Pro Xaa Xaa Pro Phe Pro Xaa Pro Xaa
1               5                   10                  15

Xaa Pro Xaa His
        20
```

PEPTIDE, MAGNETIC PEPTIDE AND METHOD FOR DETECTING CELIAC DISEASE

This application is the U.S. National Phase of International Patent Application Serial No. PCT/ES2015/070097, filed Feb. 16, 2015, which claims priority to Spanish Patent Application No. P201430198, filed on Feb. 14, 2014. The contents of the foregoing applications are incorporated herein by reference in their entireties.

FIELD OF THE INVENTION

The present invention relates to a method for detecting coeliac disease using a peptide immobilised on magnetic particles.

STATE OF THE PRIOR ART

Coeliac Disease (CD) is a form of enteropathy that affects genetically predisposed individuals, on coming into contact with gluten-containing foods. This determines the appearance of a characteristic histological lesion, which in other more serious forms causes atrophy of the intestinal villi. This can give rise to a nutrient malabsorption defect (immediate principles, mineral salts and vitamins) that leads to numerous deficiencies responsible for a broad spectrum of clinical manifestations such as osteomalacia (softening of bones due to loss of calcareous salts), stomach ulcers and malign processes such as gastrointestinal neoplasia.

CD may occur at any age and is accompanied by a wide variety of clinical manifestations, although in many cases the disease is asymptomatic. These premises make the role of the paediatrician and family doctor in primary health care particularly relevant in early diagnosis, thereby avoiding the onset of long-term serious complications.

CD consists of a permanent intolerance to gluten proteins found in wheat (gliadin), rye (secalin), barley (hordein) and triticale (wheat and rye hybrid).

Although this disease was considered rare in many European countries, the availability of non-invasive, sensitive serological assays has enabled the detection of coeliac disease in the population in general.

The prevalence of coeliac disease in the world is estimated at 1/266 and in Spain ranges between 1/118 in the paediatric population and 1/389 in the adult population. However, the epidemiology of CD has the characteristics of an iceberg, as this prevalence could be much higher, since a significant percentage of cases remain undetected. It is estimated that for each diagnosed patient there are between 5 and 10 who are not. Therefore, according to different epidemiological studies carried out worldwide, CD without classic symptomatology is more frequent than the symptomatic form, due to which its early detection represents a challenge for the healthcare system.

Initially, the detection of coeliac disease was based on a malabsorption assay using D-xylose. Later, serological assays for anti-gliadin antibodies (AGA) and antiendomysial antibodies (AMA) began to be used. After that, the detection of anti-tissue transglutaminase antibodies 2($ATG_2$) was incorporated and, more recently, of anti-peptide gliadin deaminated antibodies (APDG).

Serum markers are of great use as CD indicators, although an intestinal biopsy continues to be the definitive method for establishing the diagnosis. Such markers help to select individuals with the highest probability of developing CD and are particularly useful in individuals without gastrointestinal symptoms, in those with diseases associated with CD and for controlling first-degree relatives of diagnosed patients. However, it must be borne in mind that the negativity of these markers does not definitively exclude the diagnosis and at times more advanced tests are required (genetic study) in those cases where there is a high suspicion of diagnosis.

Anti-gliadin antibodies (AGA) were the first to be used, as described in Stern et al., *Validations and standardization of serological screening tests for coelic disease in* 1996, 3rd EMRC/ESPGAN Workshop, Dec. 5-8, 1996, Molsheim, France, pages 9-24. They both belong to class IgA and IgG. Class IgA are preferably used and their effectiveness in CD screening is greater in children than in adults.

Antiendomysial antibodies (EMA) also belong to class IgA. Their sensitivity and specificity are variable according to age. According to the document *Early diagnosis of coeliac disease,* Ministry of Health and Consumer Affairs, Madrid, 2008 (NIPO: 351-08-086-X), said antibodies have the drawback of the laboriousness of their determination and subjectiveness of their interpretation. Additionally, it is known that some CD patients have IgA deficiency, due to which said patients would obtain negative results in this test.

IgA class human anti-tissue transglutaminase antibodies ($ATG_2$) are considered sensitive, specific and very useful markers both for diagnosing and monitoring CD. Other alternatives such as combined $ATG_2$-IgA/IgG antibodies have also been disclosed. Different methods have been described in the state of the art wherein $ATG_2$ antibodies are used. For example, in the article Kergeravat et al., *Magneto immunofluorescence assay for diagnosis of celiac disease,* Anal. Chim Acta., 2013, 798, 89-96 a method is described for diagnosing CD based on the detection of anti-$ATG_2$ antibodies using the $ATG_2$ enzyme immobilised on magnetic particles and the detection was performed by means of immunofluorescence. It is described that said assay had a sensitivity of 96.6% and a specificity of 89.5%, and an efficiency of 93.8% compared to the commercial ELISA kit.

In order to avoid taking blood samples, the detection of $ATG_2$ antibodies was also disclosed, such as for example in North American patent application US-A-2008/0038760.

Subsequently, as described in Aleanzi et al., *Antibody Recognition against Native and Selectively Deamidated Gliadin Peptides,* Clin. Chem., 2001, 47, 2023-2028, the relationship between coeliac disease and APDGs of the IgG and IgA isotopes began to be studied, since in coelic disease the gliadin peptides ingested through the diet are selectively deaminated in the intestine by the $TG_2$ enzyme, such that glutamin, $H_2NCOCH_2CH(NH_2)COOH$, is transformed by said enzyme in glutamic acid, $HOOCCH_2CH(NH_2)COOH$. This selective deamination may be the event that triggers the immune response to gluten in genetically predisposed individuals. In Schwertz et al., *Serologic Assay Based on Gliadin-Related Nonapeptides as a Highly Sensitive and Specific Diagnostic Aid in Celiac Disease,* Clin. Chem., 2004, 50, 2370-2375, nonapeptides derived from gliadin which are recognised by the antibodies of patients with CD are described. It is also described that none of the assayed deaminated octadecapeptides was a better epitope than short-chain peptides. It also describes that none of the assayed deaminated octadecapeptides was a better epitope than short-chain peptides.

In the state of the art, methods have been described to detect these APDG antibodies. Said methods are based on ELISA assays using optical detection, such as for example that described in Sakly et al., *Performance of anti-deamidated gliadin peptides antibodies in celiac disease diagno-* sis, Clin. Res. Hepatol. Gastroenterol., 2012, 36, 598-603, or an immunofluorimetric assay such as that described in Ankelo et al., *Antibody responses to deamidated gliadin peptide show high specificity and parallel antibodies to tissue transglutaminase in developing coeliac disease, Clin. Exp. Immunol.*, 2007, 150, 285-293.

In the state of the art, new CD detection methods continue to be disclosed. For example, in international patent application WO-A.2009/131909 a method for detecting CD in an individual wherein an antigen formed from a deaminated recombinant gliadin bonded to a tag such as the glutathione-S-transferase protein or His-tag, which may include tissular transaminase. Said antigen is immobilised on magnetic particles modified with carboxyl groups.

Recently, the use of anti-beta-lactoglobulin antibodies in the diagnosis and monitoring of CD through the analysis of a blood sample of the patient has been disclosed in WO-A.2013/083866.

Despite the solutions described in the state of the art, there is still a need to provide a simple, quick method with improved selectivity and specificity for detecting coeliac disease and overcome, at least partially, the drawbacks of the methods of the state of the art.

OBJECT OF THE INVENTION

The object of the present invention is a peptide.

Also forming part of the object of the invention is a magnetic peptide that comprises said peptide and a particulated magnetic complex.

Also forming part of the object of the invention is an immunosensor that comprises said magnetic peptide.

Also forming part of the object of the invention is a method for detecting coeliac disease.

Also forming part of the object of the invention is the use of said peptide to detect coeliac disease.

Also forming part of the object of the invention is the use of said magnetic peptide to detect coeliac disease.

Also forming part of the object of the invention is the use of said immunosensor to detect coeliac disease.

Also forming part of the object of the invention is a kit for detecting coeliac disease.

DETAILED DESCRIPTION OF THE INVENTION

The object of the present invention is to provide a linear peptide that responds to the general formula (I):

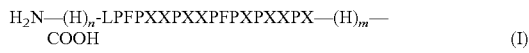

(SEQ ID NO: 62)
wherein:
X is Q or E equally and at least one X is E, and
wherein:
n is comprised between 2 and 20, and m is 0, or
m is comprised between 2 and 20, and n is 0.

Such peptide is appropriate for use in a method for detecting CD once immobilised with a particulated magnetic complex.

The authors of the present invention have developed a method for detecting coeliac disease wherein the peptide of the general formula (I) immobilised on a particulated magnetic complex is used as an antigen and which, surprisingly, enables detection with high sensitivity and specificity, and is also a simple and quick method.

The abbreviations used for the amino acids in this description are based on the regulation of the Committee for Biochemical Nomenclature of the IUPAC-IUB, as described in the article *Nomenclature and symbolism for amino acids and peptides*, Pure & Appl. Chem., 1984, 56(5), 595-624. Therefore, H is L-histidine, L is L-leucine, F is L-phenylalanine, P is L-proline, Q is L-glutamine and E is glutamic acid.

In the present description and in the claims, the singular forms "a/an" and "the" include a reference in plural, unless the context indicates the opposite.

Peptide

The peptide of the invention responds to the general formula (I):

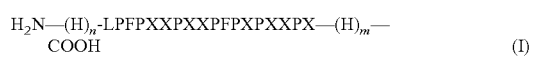

(SEQ ID NO: 62)
wherein:
X is Q or E equally and at least one X is E, and
wherein:
n is comprised between 2 and 20, and m is 0, or
m is comprised between 2 and 20, and n is 0.

Said peptides, defined by the sequences SEQ_ID_NO: 1 to 38, are derived from deaminated gliadin peptides to which a queue of between 2 and 20 histidines (H) have been added at the N-terminal end, wherein the amino group (NH$_2$) is located, or at the C-terminal end, wherein the carboxyl group (COOH) is located, preferably n and m are comprised between 4 and 15, more preferably between 6 and 10, and even more preferably between 6 and 8.

More preferably, the peptide of the invention responds to the general formula (I), wherein m is zero (0) and n is comprised between 2 and 20, more preferably between 4 and 15, more preferably between 6 and 10 and even more preferably between 6 and 8.

In another preferred embodiment, the peptide of the invention responds to the general formula (I), wherein n is zero (0) and m is between 2 and 20, more preferably between 4 and 15, more preferably between 6 and 10 and even more preferably between 6 and 8.

More preferably, the peptide of the invention is selected from the group formed by:

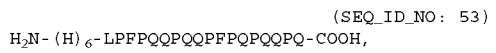

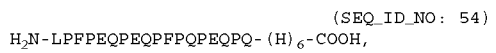

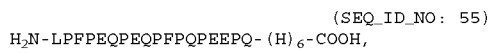

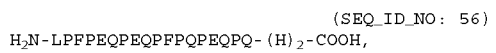

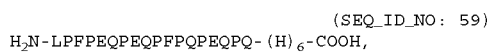

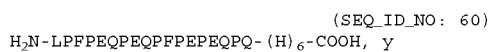

```
                                                  (SEQ_ID_NO: 61)
H₂N-(H)₂-LPFPEQPEQPFPQPEQPQ-COOH.
```

Even more preferably, the peptide of the invention is selected from the group formed by:

```
                                                  (SEQ_ID_NO: 39)
H₂N-(H)₆-LPFPEQPEQPFPQPEQPQ-COOH, (SEQ_ID_NO: 53)
H₂N-(H)₆-LPFPQQPQQPFPQPQQPQ-COOH, (SEQ_ID_NO: 54)
H₂N-LPFPEQPEQPFPQPEQPQ-(H)₆-COOH, (SEQ_ID_NO: 57)
H₂N-(H)₄-LPFPEQPEQPFPQPEQPQ-COOH, (SEQ_ID_NO: 58)
H₂N-(H)₁₀-LPFPEQPEQPFPQPEQPQ-COOH, (SEQ_ID_NO: 59)
H₂N-LPFPEQPEQPFPQPEQPQ-(H)₆-COOH, y (SEQ_ID_NO: 61)
H₂N-(H)₂-LPFPEQPEQPFPQPEQPQ-COOH.
```

Even more preferably, the peptide of the invention is selected from the group formed by:

```
                                                  (SEQ_ID_NO: 39)
H₂N-(H)₆-LPFPEQPEQPFPQPEQPQ-COOH, (SEQ_ID_NO: 54)
H₂N-LPFPEQPEQPFPQPEQPQ-(H)₆-COOH, y (SEQ_ID_NO: 58)
H₂N-(H)₁₀-LPFPEQPEQPFPQPEQPQ-COOH.
```

In the article by Schwertz et al., mentioned earlier, 12 deaminated octadecapeptides, without a histidine tag, are described, which are defined by the following sequences:

| Deaminated peptide | SEQ_ID_NO: |
|---|---|
| H₂N-LPFPEQPEQPFPQPEQPQ-COOH | 40 |
| H₂N-LPFPQQPEQPFPQPEQPQ-COOH | 41 |
| H₂N-LPFPEQPQQPFPQPEQPQ-COOH | 42 |
| H₂N-LPFPEQPEQPFPQPQQPQ-COOH | 43 |
| H₂N-LPFPQQPQQPFPQPQQPE-COOH | 44 |
| H₂N-LPFPQQPQQPFPQPQEPQ-COOH | 45 |
| H₂N-LPFPQQPQQPFPQPEQPQ-COOH | 46 |
| H₂N-LPFPQQPQQPFPEPQQPQ-COOH | 47 |
| H₂N-LPFPQQPQEPFPQPQQPQ-COOH | 48 |
| H₂N-LPFPQQPEQPFPQPQQPQ-COOH | 49 |
| H₂N-LPFPQEPQQPFPQPQQPQ-COOH | 50 |
| H₂N-LPFPEQPQQPFPQPQQPQ-COOH | 51 |

Such peptides conveniently modified with a histidine tag are also appropriate for being used in the method of the invention. Preferably, they comprise between 2 and 20 histidines (H) at the N-terminal end, i.e. n is comprised between 2 and 20 and m is zero (0), or at the C-terminal end, i.e. m is comprised between 2 and 20 and n is zero (0), preferably n and m are comprised between 4 and 15, more preferably between 6 and 10 and even more preferably between 6 and 8. More preferably, said peptides comprise a histidine tag wherein m is zero (0) and n is comprised between 2 and 20, more preferably between 4 and 15, more preferably between 6 and 10 and even more preferably between 6 and 8.

In the article by Ankelo et al., mentioned earlier, two peptide derivatives of the peptide defined by the formula (SEQ_ID_NO_40), without histidine tag, are described. One of them is modified with biotin at the N-terminal end, and at the other C-terminal end, having included an additional lysine residue to facilitate the incorporation of biotin, H₂N-LPFPEQPEQPFPQPEQPQK—COOH (SEQ_ID_NO: 52). The incorporation of biotin in said peptides is due to the use of plates coated with streptavidin protein, which forms a very strong affinity complex with the biotin, whereupon the peptide is immobilised.

The peptides described in the invention are formed by between 20 and 38 amino acids that makes them appropriate for being prepared using the usual solid-phase peptide synthesis procedures such as, for example, those described by, for example, those described by R. B. Merrifield, J.Am. Chem.Soc., 1963, 85, 2149-2154. They can also be commercially acquired from, for example, the companies Eurogentec, S. A. (Seraing, Bélgica) or GenScript (Piscataway, USA).

Magnetic Peptide

Also forming part of the invention is a magnetic peptide that comprises:

a) the peptide with the general formula (I):

$$H_2N-(H)_n\text{-LPFPXXPXXPFPXPXXPX}-(H)_m-COOH \quad (I)$$

(SEQ ID NO: 62)

wherein:

X is equally Q or E and at least one X is E, and wherein:

n is comprised between 2 and 20, and m is 0, or m is comprised between 2 and 20, and is 0, and b) a particulated magnetic complex with the general formula (II):

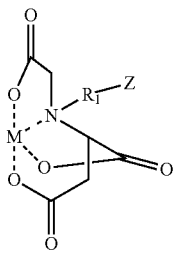

(II)

wherein:
Z is a magnetic polymer particle covalently bonded to the carboxymethylated aspartate ligand through $R_1$,
$R_1$ is an arm connecting the nitrogen atom of the carboxymethylated aspartate ligand to the magnetic polymer particle Z and
M is an ion of a transition metal with a coordination number 6.

The peptide of the invention is immobilised on a magnetic polymer particle (hereinafter PM) by means of the histidine tag that forms complexes with the transition metal, thereby completing the coordination sphere of said metal. In accordance with the disclosures of the state of the art, for example, North American patent U.S. Pat. No. 5,962,641, the coordination complex formed between a peptide that contains a histidine tag and the transition metal can be classified as very strong. In the context of this invention, it is considered that the binding of the peptide with the transition metal is substantially a coordination complex that does not include covalent bonds.

Eventually, the particulated magnetic complex includes countercations, for example, $Na^+$ or $Li^+$, to offset the excessively negative charges of the carboxymethylated aspartate ligand that forms part thereof.

Magnetic Polymer Particle

In the context of the invention, magnetic polymer particle (MP) is understood to be a particle formed by a polymer that contains a superparamagnetic substance. In this manner, the MPs are displaceable due to the effect of a magnetic field, but are not permanently magnetisable. Functionalised magnetic polymer particle is understood to be a MP that includes functional groups preferably disposed on the surface thereof that enable the subsequent anchoring of other molecules.

MPs are usually formed by combinations of vinyl polymers (for example, styrene), acrylates and/or methacrylates. The polymer can be reticulated by means of the incorporation of reticulating agents such as comonomers, for example, ethyleneglycol divinylbenzene or dimethacrylate. Preferably, the polymer is a reticulated styrenic polymer, for example, a surface-functionalised polymer formed by styrene and divinylbenzene or a surface-functionalised reticulated (meth)acrylated polymer with a comonomer that contains, for example, an epoxy group. The person skilled in the art has no trouble determining the appropriate amounts of each of the monomers involved in the formation of the polymer particles. For example, patent application WO-A-00/61647 discloses procedures for preparing polymer particles, which may include magnetic materials, among others.

The functionalisation of the surface of polymer particles makes it possible to obtain functionalised MPs that facilitate the coupling of the carboxymethylate aspartate to said particles. Said functionalisation can be carried out by means of the incorporation of, for example, carboxyl, nitro, amino, tosyl, epoxy or thiol groups. Often, functionalised MPs are prepared from styrene polymers that are nitrated to introduce a nitro group on the surface thereof. The reduction of the nitro group to an amino group using conventional means makes it possible to have functionalised MPs with amino groups that can easily react with other groups, for example, halo derivatives.

Iron oxides can be used as a superparamagnetic substance, such as for example, magnetite ($Fe_3O_4$). Different procedures have been described to prepare MPs, such as for example that found in patent U.S. Pat. No. 4,654,267.

The MPs of the invention typically have an average diameter comprised between 0.3 and 100 microns, preferably between 0.5 and 50 micron, more preferably between 0.8 and 8 microns, and even more preferably between 0.8 and 1.2 microns.

Usually, MPs are substantially spherical and substantially monodisperse. Substantially monodisperse is understood to be that, for a plurality of particles, they have a coefficient of variation (CV) of at least 20%, preferably less than 15%, more preferably less than 10% and more preferably no more than 8%, for example, between 2% and 5%. The coefficient of variation is determined as a percentage as CV=(100× standard deviation)/average.

Due to its small size and substantially spherical geometry, a large number of biomolecules can be immobilised on the surface of these functionalised MPs. The use of these particles has a series of advantages, namely: improved assay sensitivity, reduced possible matrix effect of the sample, avoidance of complex pretreatment stages, reduced reaction times and possibility of manipulating them on different platforms through the application of a permanent magnetic field, such as for example on the surface of the working electrode or on a microtitration plate.

Carboxymethylated Aspartate Ligand

The carboxymethylated aspartate is usually used in the purification of proteins using the immobilised metal affinity chromatography technique (IMAC), as described, for example, in patent application WO-A-98/06739.

The carboxymethylated aspartate ligand is covalently bonded to the magnetic polymer particle Z through the connecting arm $R_1$.

Said bond can be executed by means of different procedures. For example, it can be executed by reaction between and electrophile group of the functionalised ligand (for example, a haloalkylene or an alkylenecarboxylic group) and a nucleophile group of Z (for example, an amino group, aminoalkylene, hydroxy, hydroxyalkylene, thiol or thiolalkylene). It can also be executed by reaction between a nucleophile group of the functionalised ligand (for example, an aminoalkylene, hydroxyalkylene or thiolalkylene group) and an electrophile group of Z (for example, a haloalkylene group or a carboxylic group). Preferably, the reaction is executed between ligand modified with a nucleophile group and an electrophile group of Z, such as that described, for example, in the examples of patent application WO-A-2005/089933. To this end, the ligand can be functionalised by introducing a nucleophile group, such as the amino group, so that it can react with an electrophile group of the Z particle, for example, a methylene group that includes a halogen atom such as bromine. The reactive group of the Z particle is preferably found on the surface thereof and is the result of the functionalisation of the polymer that constitutes said particle, as expounded previously.

Preferably, the $R_1$ group, which is the arm connecting the nitrogen atom of the carboxymethylated aspartate ligand and the surface of the particle, consists of a chain of between 3 and 20 atoms, more preferably between 5 and 20 atoms, and even more preferably between 6 and 20 atoms. The $R_1$ connecting arm between the nitrogen atom of the carboxymethylated aspartate ligand and the Z particle is preferably selected from -alkylene-NH—, -alkylene-CO—NH—, -alkylene-NH—CO—, -alkylene-O—, -alkylene-CO—O—, -alkylene-O—CO—, -alkylene-S—, -alkylene-CO—S—, -alkylene-S—CO—, -alkylene-NH-alkylene-$R_2$, -alkylene-NH—CO-alkylene-$R_2$, -alkylene-CO—NH-alkylene-$R_2$, -alkylene-O-alkylene-$R_2$, -alkylene-O—CO-alkylene-$R_2$, -alkylene-CO—O-alkylene-$R_2$, -alkylene-S-alkylene-$R_2$, -alkylene-S—CO-alkylene-$R_2$, -alkylene-CO—S-alkylene-$R_2$, -hydroxyalkylene-NH—, -hydroxyalkylene-CO—NH—, -hydroxyalkylene-NH—CO—, -hydroxyalkylene-O—, -hydroxyalkylene-CO—O—, -hydroxyalkylene-O—CO—, -hydroxyalkylene-S—, -hydroxyalkylene-CO—S—, -hydroxyalkylene-S—CO—, -hydroxyalkylene-NH-alkylene-$R_2$, -hydroxyalkylene-NH—CO-alkylene-$R_2$, -hydroxyalkylene-CO—NH-alkylene-$R_2$, -hydroxyalkylene-O-alkylene-$R_2$, -hydroxyalkylene-O—CO-alkylene-$R_2$, -hydroxyalkylene-CO—O-alkylene-$R_2$, -hydroxyalkylene-S-alkylene-$R_2$, -hydroxyalkylene-S—CO-alkylene-$R_2$, hydroxyalkylene-CO—S-alkylene-$R_2$, -alkylene-NH-hydroxyalkylene-$R_2$, -alkylene-NH—CO-hydroxyalkylene-$R_2$, -alkylene-CO—NH-hydroxyalkylene-$R_2$, -alkylene-O-hydroxyalkylene-$R_2$, -alkylene-O—CO-hydroxyalkylene-$R_2$, -alkylene-CO—O-hydroxyalkylene-$R_2$, -alkylene-S-hydroxyalkylene-$R_2$, -alkylene-S—CO-hydroxyalkylene-$R_2$, and -alkylene-CO—S-hydroxyalkylene-$R_2$, wherein $R_2$ is a functional bonding group and is preferably O, S or NH, and more preferably NH.

More preferably, $R_1$ is selected from -alkylene-NH—, -alkylene-CO—NH—, -alkylene-NH—CO—, -alkylene-O—, -alkylene-CO—O—, -alkylene-O—CO—, -alkylene-NH-alkylene-$R_2$, -alkylene-NH—CO-alkylene-$R_2$, -alkylene-CO—NH-alkylene-$R_2$, -alkylene-O-alkylene-$R_2$, -alkylene-$R_2$, -alkylene-O—CO-alkylene-$R_2$, -alkylene-CO—O-alkylene-$R_2$, -hydroxyalkylene-NH—, -hydroxyalkylene-CO—NH—, -hydroxyalkylene-NH—CO—, -hydroxyalkylene-O—, -hydroxyalkylene-CO—O—, -hydroxyalkylene-O—CO—, -hydroxyalkylene-NH-alkylene-$R_2$, -hydroxyalkylene-NH—CO-alkylene-$R_2$, -hydroxyalkylene-CO—NH-alkylene-$R_2$, -hydroxyalkylene-O-alkylene-$R_2$, -hydroxyalkylene-O—CO-alkylene-$R_2$, -hydroxyalkylene-CO—O-alkylene-$R_2$, -alkylene-NH-hydroxyalkylene-$R_2$, -alkylene-NH—CO-hydroxyalkylene-$R_2$, -alkylene-CO—NH-hydroxyalkylene-$R_2$, -alkylene-O-hydroxyalkylene-$R_2$, -alkylene-O—CO-hydroxyalkylene-$R_2$, and -alkylene-CO—O-hydroxyalkylene-$R_2$. Aún más preferiblemente $R_1$ se selecciona de entre -alkylene-NH-alkylene-$R_2$, -alkylene-NH—CO-alkylene-$R_2$, -alkylene-CO—NH-alkylene-$R_2$, -alkylene-O-alkylene-$R_2$, -alkylene-O—CO-alkylene-$R_2$, and -alkylene-CO—O-alkylene-$R_2$; still more preferably from -alkylene-NH-alkylene-$R_2$,y-alkylene-O-alkylene-$R_2$; even more preferably it is -alkylene-NH-alkylene-$R_2$, wherein $R_2$ is a functional bonding group and is preferably O, S or NH, and more preferably NH. Even more preferably, $R_1$ is the —$(CH_2)_x$—NH—$(CH_2)_y$—NH group, wherein x and y are comprised between 1 and 6, more preferably between 3 and 5, wherein the $(CH_2)_x$ group is bonded to the nitrogen atom of the carboxymethylated aspartate ligand and the NH group disposed on the right is that which is bonded to the magnetic polymer particle Z.

The Transition Metal

The transition metal M with coordination number 6 is preferably selected from the group formed by Ni, Fe, Ga, Mn, Co, Cu and Zn, more preferably by Ni, Fe, Mn and Co, and more preferably Co. The transition metal ion M preferably has an oxidation state of +2 or +3, more preferably +2. In a particularly preferred manner, the transition metal ion is $Co^{+2}$. In the magnetic polymer particle of formula (II) the metal M is complexed by the three carboxylate groups and the amino group of the carboxymethylated aspartate ligand. In order to the complex between the transition metal and the carboxymethylated aspartate ligand, methods well known by the person skilled in the art may be used, for example, exposing a metal salt to the ligand. For example, it can be separated by suspending the magnetic polymer particles that comprise the ligand in water and adding a solution of a salt of the corresponding metal. The following salts may be used, among others: $CoCl_2$, $CuSO_4$, $FeCl_3$, $GaCl_2$, $GaCl_3$, $MnSO_4$, $NiCl_2$, or $ZnCl_2$.

A particularly preferred particulated magnetic complex is that described in Example 4 of patent application WO-A-2007/089933. In such example MPs that comprise the carboxymethyl aspartate ligand and which are obtained in accordance with the following process are charged with cobalt chloride (II): magnetic styrene particles functionalised with alyl groups with a bromation agent are made to react; next, said bromated particles are made to react with the N-aminopentyl-N-diethyl etoxycarboxymethylaspartate and, lastly, the ester groups are hydrolised. Said sequence of reactions is visualised in the following diagram:

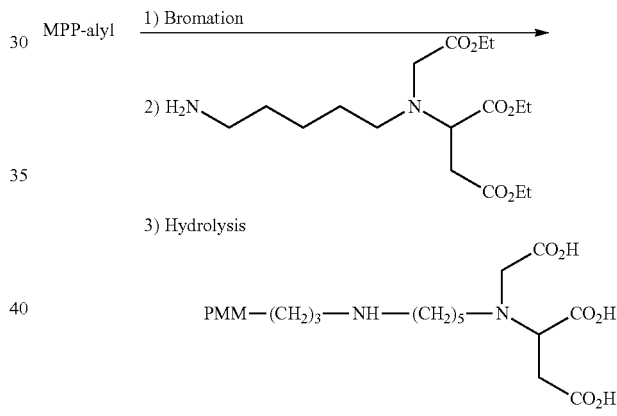

The particulated magnetic complexes that form part of the magnetic peptide of the invention can be prepared using identical procedures to those previously described or can be commercially acquired through the companies Clontech, Invitrogen Dynal and Merck Millipore. Especially preferred are the particulated magnetic complexes called Dynabeads®TALON®, which can be commercially obtained through the company Invitrogen Dynal (Oslo, Norway) and which respond to the particulated magnetic complex obtained in Example 4 of patent application WO-A-2007/089933.

The magnetic peptide is obtained by immobilising the peptide of the invention on the particulated magnetic complex.

Such immobilisation can be carried out, for example, under the conditions described by the manufacturer for the product Dynabeads®TALON®, for example, under the Manuals and Protocols section of the website http://lifetechnologies.com/ or in the technical leaflet thereof. It is incubation process of the peptide with said particulated magnetic complex in an immobilisation buffer formed by sodium phosphate 0.05 M, pH 8, NaCl 0.3 M and 0.01% of Tween®

20 (sorbitan monolaurate with 20 moles of ethylene oxide) for a period of time of 10 minutes at a temperature of 25° C.

The efficiency of immobilisation to obtain the magnetic peptide of the invention is practically quantitative.

In a particularly preferred embodiment, the magnetic peptide of the invention comprises the peptide defined by the sequence SEQ_ID_NO: 39, Z are magnetic polystyrene particles, $R_1$ is the —$(CH_2)_5$—NH—$(CH_2)_3$—NH group and M is $Co^{2+}$, wherein the $(CH_2)_5$ group is bonded to the nitrogen atom of the carboxymethylated aspartate ligand and the NH group located on the right is that which is bonded to the magnetic polymer particle Z.

Immunosensor

An immunosensor that comprises the magnetic peptide of the invention and a transducer with a magnet coupled to or integrated therewith forms part of the invention.

In general, an immunosensor consists of a biological recognition element (antigen or antibody) and a transducer (electrochemical: potentiometric, amperometric or conductimetric; optical; piezoelectric; thermometric; magnetic; micromechanical). Some of these are defined as direct, wherein a physical change is detected during the formation of the complex and others as indirect, wherein the signal is generated by a label (generally enzymatic).

Within the framework of the invention, the transducer is preferably electrochemical or optical. In a preferred embodiment, the method is carried out using an immunosensor that comprises an electrochemical transducer which includes a magnet.

In this specific case, the electrochemical measurements, based on three types of analytical signals (potential, current and charge), are made in an electrochemical cell consisting of two or more electrodes and electronically associated to control and measure potential and current. In the case of a cell composed of two electrodes submerged in a solution, on applying an external potential between said electrodes, the circulation of an electric current derived from the electrochemical processes that occur in the electrode-solution interface takes place. The origin of this current may be the transfer of charge due to chemical reactions (faradaic processes) or the reorganisation of the charge in the interphase (non-faradaic processes).

Detection Method

The coeliac disease detection method consists of what is called an immunoassay which, within the framework of the present invention, includes sets of analytical immunochemical laboratory techniques which have the use of immune complexes in common, i.e. the result of making antibodies interact with antigens, for the purpose of detecting and/or quantifying analytes in samples. The selectivity of the antibodies to bond with their ligands allows these biomolecules to be used in highly specific analytical methods in the case of complex matrices such as blood, plasma or urine. By combining the selectivity of the antibody-antigen interactions with a wide range of antibodies preformed during the immunisation processes of host animals and the availability of numerous easily detectable labels (radioisotopes, absorbance, fluorescence or enzymatically or electrochemically induced chemiluminescence), the immunoassays can be designed for a wide range of analytes with extraordinarily low detection limits. Examples of these limits are concentration levels of hormones, enzymes, viruses, tumoral and bacterial antigens close to $10^{-12}$-$10^{-9}$ mol/L.

Non-limiting illustrative examples of labels include radioactive elements (for example, sulphur, iodine, etc.); enzymes (for example, peroxidase, glycosidase, alkaline phosphatase, HRP peroxidase, glucose-6-phosphate dehydrogenase, β-galactosidase, β-glucosidase, β-glucuronidase, etc.); fluorescent (for example, fluorescein, rhodamine, etc.), phosphorescent or chemiluminiscent compounds or dyes (for example, dioxetanes, acrydines, phenantridines, rutenes, luminol, etc.). The selection of a specific label is not critical, provided that it is capable of producing a signal on its own or jointly with one or more additional substances. Therefore, the complex formed can be detected or visualised using any appropriate technique, depending on the label chosen, well known by the persons skilled in the art, using the appropriate devices, for example, using techniques based on radioactive, electrochemical, colorimetric, fluorometric (chemi)luminescent, etc., all known by the persons skilled in the art.

By way of example, when the labelled is an enzyme, the detection of the complex (antigen-antibody)/label can be performed by placing said complex in contact with an appropriate substance and, optionally, with the appropriate enzymatic activators and/or agents. Illustrative examples of said substrates include for:

alkaline phosphatase: substrates based on p-nitrophenyl phosphate (p-NPP) or 2-(5-chloro-2'-phosphoryloxyphenyl)-6-chloro-4-(3H)quinazolinone (CPPCQ);

peroxidases: substrates based on 2,2-azinobis(3-ethylbenzothiazoline-6-sulphonic) acid (ABTS), o-phenylendiamine (OPT), 3,3',5,5'-tetrametylbenzidine (TMB), o-dianisidine, 5-aminosalicylic acid, 3-dimethylaminobenzoic acid (DMAB) and 3-methyl-2-benzothiazolinhydrazone (MBTH), 3-amino-9ethylcarbazol (AEC) and 3,3'-diaminobenzidine tetrachloride (DAB), 4-hydroxy-3-methoxyfenylacetic acid, reduced phenoxazines and reduced benzothiazines;

glycosidases: substrates based on o-nitrophenyl-β-D-galactoside (o-NPG), p-nitrophenyl-β-D-galactoside and 4-methylumbeliphenyl-β-D-galactoside (MUG) for β-D-galactosidase.

Non-limiting illustrative examples of appropriate immunoassay formats for putting the methods of the present invention into practice include ELISA (enzyme-linked immunoabsorbent assay), DAS-ELISA ("Double Antibody Sandwich-ELISA"), DELFIA (dissociation-enhanced lanthanide fluoroimmunoassay), FPIA (fluorescence polarisation immunoassay), CMIA (chemiluminescent magnetic immunoassay), IRMA (heterogeneous and non-competitive radioimmunoassay), MEIA (microparticle-based immunoassay), luminoimmunoassays, immunocytochemical and immunohistochemical techniques, colloidal precipitation-based assays (dipsticks). Non-limiting illustrative examples of execution platforms of these immunoassays include microtritation plates, biochips, biosensors (for example immunosensors) or microarrays, lab-on-a-chip, dipsticks, immunoassays based on lateral flow chromatography using immunochromatographic strips and, in all cases, to which a magnet has been coupled or integrated.

Therefore, also forming part of the object of the invention is a method for detecting coeliac disease that comprises the following stages:

1) incubating a suspension of the magnetic peptide of the invention with a serum or blood sample of an individual, 2) adding anti-human serum-HRP, selected from anti-human IgA-HRP and anti-human IgG-HRP, to the suspension incubated in point 1) and incubating the suspension obtained, and 3) measuring the electrochemical or optical signal obtained from the suspension obtained in point 2).

In stage 2) anti-human serum-HRP antibodies are used which are preferably anti-human IgA-HRP, wherein HRP corresponds to the horseradish peroxidase enzyme, because it has advantages with respect to other antibodies. HRP peroxidase is a 40 kDa protein that catalyses the oxidation of substrates by means of hydrogen peroxide, giving rise to a coloured or fluorescent product or light emission as a by-product. Said enzyme works optimally at an approximately neutral pH and can be inhibited by cyanides, sulphides and azides. The antibody-HRP conjugates are superior to the antibody-alkaline phosphatase conjugates with respect to the specific activities of the enzyme and the antibody. Additionally, said peroxidase has a high enzyme speed, good stability, low cost and broad availability, due to which it is one of the enzymes to be chosen for most applications.

The method of the invention is an immunoassay in which the antigen immobilised in the magnetic particle (magnetic peptide of the invention) captures the antibody to be detected (present in the serum or blood of an individual) and the immunocomplex thus formed is subsequently bonded to an antibody labelled with the enzyme (anti-human IgA-HRP), which generates an electrochemical or optical signal directly proportional to the antibody concentration in the sample, once all the immunocomplex is capture don a platform for its detection as of the application of a permanent magnetic field. Incubation can be carried out in Eppendorff tubes using between 50 and 100 µL, preferably between 60 and 80 µL of a magnetic peptide solution of the invention at a concentration of 0.2 mg/mL. The incubation of the suspension of the magnetic peptide with a serum or blood sample of an individual who may be suffering from CD is usually carried out at a temperature comprised between 20° C. and 27° C., preferably around 25° C., for a period of time comprised between 20 and 45 minutes, preferably between 25 and 35 minutes, and more preferably around 30 minutes.

The incubation of the suspension obtained after adding anti-human IgA-HRP is usually carried out at a temperature comprised between 20° C. and 27° C., preferably around 25° C., for a period of time comprised between 20 and 45 minutes, preferably between 25 and 35 minutes, and even more preferably around 30 minutes.

After each stage, a permanent magnetic field is applied to capture the magnetic particles and wash them with PBS buffer, following procedures well known by the skilled person in the art.

The measurement of the electrochemical or optical signal can be made by measuring a signal generated by the HRP enzyme by reaction with hydrogen peroxide as a substrate and mediator selected from a group formed by phenol, o-phenylendiamine (OPD), 3,3',5,5'-tetramethylbencidine (TMB), hydroquinone, p-chlorophenol, pirocatecol and p-aminophenol. Preferably, hydroquinone is used as a mediator for electrochemical detection and TMB for optical detection.

Forming part of the object of the invention is the use of the peptide of the invention to detect coeliac disease.

Also forming part of the object of the invention is the use of the magnetic peptide of the invention to detect coeliac disease.

Also forming part of the object of the invention is the use of the immunosensor to detect coeliac disease Also forming part of the invention is a kit for detecting coeliac disease that comprises the magnetic peptide of the invention.

The kit of the invention includes, in addition to the magnetic peptide, an adequate immunoassay or platform for putting the method for detecting coeliac disease into practice. Non-limiting illustrative examples of adequate immunoassay formats for putting the methods of the present invention into practice include ELISA (enzyme-linked immunoabsorbent assay), DAS-ELISA (Double Antibody Sandwich-ELISA), DELFIA (dissociation-enhanced lanthanide fluoroimmunoassay), FPIA (fluorescence polarisation immunoassay), CMIA (chemiluminescent magnetic immunoassay), IRMA (heterogeneous and non-competitive radioimmunoassay), MEIA (microparticle-based immunoassay), luminoimmunoassays, immunocytochemical and immuno-histochemical techniques, assays based on colloidal precipitation (dipsticks). Non-limiting illustrative examples of platforms for the performance of these immunoassays include microtritation plates, biochips, biosensors (for example, immunosensors) or microarrays, lab-on-a-chip, dipsticks, lateral flow chromatography using immunochromatographic strips and, in all cases, to which a magnet has been coupled or integrated.

Detection Assays

Serums of patients clinically classified as coeliacs and non-coeliacs, in both cases confirmed by biopsy, by means of the electrochemical immunosensor of the invention destined for the individual detection of anti-human APDG-IgA were evaluated. These serums were also analysed using an optical ELISA. In addition, an electrochemical immunosensor obtained in the Example of reference 1, wherein the peptide of the invention was covalently bonded to magnetic polymer particles functionalised with tosyl groups, was also assayed.

The results of each immunosensor were analysed using sensitivity and specificity data.

The sensitivity corresponds to the probability of obtaining a positive result when the individual has the disease and is defined by the following equation:

$$\text{sensitivity} = \frac{tp}{tp + fn}$$

wherein TP corresponds to a true positive sample and fn corresponds to a false negative sample.

Furthermore, specificity is calculated as the probability of obtaining a negative result when the individual has the disease and is defined by the following equation:

$$\text{specificity} = \frac{tn}{tn + fp}$$

wherein tn corresponds to a true negative sample and fp corresponds to a false positive sample.

An ideal diagnostic test should have SE ES as close as possible to 100%. In practice, tests with SE and ES below 80% should be doubted.

It has been observed that the immunosensor with the magnetic peptide of the invention has greatest electrochemical signals for the different samples assayed and allowed greater differentiation between positive and negative samples with respect to the immunosensor obtained in the Example of reference 1, wherein the peptide of the invention was covalently bonded to magnetic polymer particles functionalised with tosyl groups. In one assay with eleven samples, seven positive and four negative, the immunosensor with the magnetic peptide of the invention presented a sensitivity of 100%, a specificity of 100% and an efficiency of 100%, while the immunosensor with the covalently bonded peptide presented a sensitivity of 86%, a specificity of 75% and an efficiency of 82%, wherein this last parameter is calculated as a percentage of the correctly positive and correctly negative results with respect to the expected reference value.

It was also observed that with the magnetic peptide of the invention 100% of the 23 patients who had CD confirmed by biopsy were discriminated. It can also be observed that, surprisingly, the magnetic peptide of the invention, which comprises the peptide of the invention and a particulated magnetic complex, makes it possible to provide a method for detecting CD with a selectivity and specificity significantly greater to that of the other detection methods described in the state of the art. In comparison with the method described in Ankelo et al., mentioned earlier, which uses the peptide defined by the sequence SEQ_ID_NO: 40 modified with biotin in a solid-phase lanthanide immunofluorometric assay, it presents greater sensitivity and specificity, 100% vs 92% and 100% vs 96%, respectively. In comparison to the method described in Schwertz et al., wherein deaminated octadecapeptides defined by SEQ_ID_NO: 40 to 51 are used, the peptide of the invention presents greater sensitivity and specifity,100% vs 85% and 100% vs 95%, respectively.

Said method constitutes a fast, cheap detection method requiring minimum manipulation and can be used in outpatient analyses, due to which the object of the invention represents a significant development in the detection of coeliac disease. Additionally, it should be noted that the electrochemical methodologies have the potentiality, compared to optical ELISA assays, of being able to develop small devices that make it possible to reduce the volume of the sample and reagents and be coupled to portable instrumentation easily transportable to different healthcare centres located far from large urban centres.

The skilled person in the art has no trouble in applying the magnetic peptide of the invention to other platforms with detection systems other than the electrochemical immunosensor or to the optical ELISA immunoassay described, such as lateral flow assays or microfluidic systems.

Following are some examples to illustrate the present invention, although they should not be considered limiting thereof.

EXAMPLES

The immobilisation of the peptides on magnetic particles was carried out using an Eppendorf ThermoMixer. Nunc polystyrene ELISA plates were used (Roskilde, Denmark). The magnetic separation of the particles was carried out using a Dynal MPC-S magnetic separator (Dynal, Noruega). A MS1 Mini-Agitator (IKA, R.F.A.) and an Eppendorf ThermoMixer were used in the incubation and washing stages. The optical and electrochemical measurements were made using TECAN Sunrise plates and with a LC-4C amperometric controller LC-4C (BAS Bioanalytical System Inc., USA).

An electrochemical cell was used consisting of a system with three independent electrodes: a m-GEC electrode (grahite-epoxy composite with magnetic connector) as the working electrode; a platinum electrode as ancillary electrode and an Ag/AgCl electrode in a 3 mol $L^{-1}$ NaCl solution as a reference (Orion 92-02-00). The m-GEC electrodes are described in Zacco et al., *Electrochemical Magnetoimmunosensing Strategy for the Detection of Pesticide Residues,* Anal. Chem., 2006, 78, 1780-1788. Ten m-GEC electrodes were prepared with their magnetic connectors and the CV % obtained from the average magnetic inductions measured in the centre of the surface of the electrode was 6.4%.

Comparative Example

Immobilisation of the Peptide on Magnetic Particles Modified With the Tosyl Group The gliadin deaminated peptide (PDG) with the sequence HHHHHHLPFPEQPEQPFPQPEQPQ (SEQ ID NO: 5) (99.2% purity) (GenScript, Cat. No. 246440) was immobilised on magnetic particles (MP) with a diameter of 1μm modified with Dynabeads MyOneTM Tosylactivated tosyl groups (Invitrogen Dynal AS, Oslo, Norway) following the protocol suggested by the manufacturer. To this end, 10 mg of MP, equivalent to a volume of 100 mg $mL^{-1}$) were washed twice using 200 μL of immobilisation buffer solution (0.05 M sodium phosphate, pH 8). Subsequently, the MPs were resuspended in 83 μL of 3 mol $L^{-1}$ ammonium sulphate, 50 μL of the concentrated PDG solution (4.3 mg $mL^{-1}$), y immobilisation buffer solution was added until completing a final volume of 250 μL. The MPs were incubated for 24 hours at 37° C. and 800 rpm. The supernatant was removed with the help of a magnet and the modified MPs were resuspended in 250 μL of blocking buffer solution and were incubated all night, under the same immobilisation conditions. The MPs were subjected to three washing stages using the washing buffer solution and were finally resuspended in the preservation buffer solution to obtain the concentrated solutions of 4 mg $mL^{-1}$ of PM-PDG, which were conserved at 4° C.

Example 1

Immobilisation of the Peptide on Dynabeads® TALON® Magnetic Particles

The deaminated gliadin peptide (PDG) with the sequence HHHHHHLPFPEQPEQPFPQPEQPQ (SEQ ID NO: 5) (99.2% purity) (GenScript, Cat. no. 246440) was immobilised on 1 μm diameter Dynabeads® TALON® magnetic particles (MP) (Invitrogen Dynal AS, Oslo, Norway) following the protocol suggested by the manufacturer. That is, 50 μL or 2 mg of MP (40 mg $mL^{-1}$) were washed in an Eppendorf tube with 650 μL of immobilisation/washing buffer solution (0.05 M sodium phosphate, pH 8, NaCl 0.3 M and 0.01% of Tween® 20, sorbitan monolaurate with 20 moles of ethylene oxide). Next, the supernatant was discarded by means of the application of a magnetic field and the MPs were incubated with 10 μL, equivalent to 4.3 μg of PDG (as of the 4,3 mg $mL^{-1}$ solution concentrated in deionised water) in a final volume of 700 μL with an immobilisation/washing buffer solution, for 10 minutes at 750 rpm and 25° C. After the incubation, the supernatant liquid of each tube was separated with the help of a magnet and the modified MPs were washed four times with 700 μL of the immobilisation/washing buffer solution and finally resuspended in PBS buffer to obtain a working solution of 4 mg/mL, as of which a diluted solution with a concentration of 0.2 mg/mL was prepared.

Example 2

Coeliac Disease Detection Assays

Detection assays were performed using an electrochemical cell and also using the ELISA optical immunoassay.

In the first case, the detection assay comprised the following stages:

1) First incubation stage: 70 μL of the 0.2 mg/mL magnetic peptide solution obtained in Example 1 were incubated with 70 μL of the positive and negative controls, and test serum, in corresponding 2 mL Eppendorf tubes at 800 rpm and 25° C. for 30 minutes. Next, the supernatant was discarded with the help of a magnetic separator and three washing stages were carried out using 100 μL of PBS buffer solution at 800 rpm and 25° C. for 3 minutes, applying the magnetic separator after each stage.

2) Second incubation stage: 140 μL of anti-human IgA-HRP diluted 1:20,000 were added and incubated at 800 rpm and 25° C. for 30 minutes. Next, the washing stages were applied in the same manner as in step (i).

3) Electrochemical measurement: in the last washing stage, the magnetic particles modified by means of the m-GEC electrodes were captured and this working electrode, together with the reference and ancillary electrodes, were immersed in 20 mL of PBS buffer solution in an electrochemical cell. The electrochemical measurement was determined by polarisation of the working electrode at E=−0.050 V (against Ag/AgCl in a 3 mol/L NaCl solution as reference electrode). The amperometric signal was based on the enzymatic activity of HRP after adding hydroquinone ($2.0 \times 10-3$ mol/L) as mediator and $H_2O_2$ ($2.0 \times 10^{-3}$ mol/L) as substrate.

The anti-human IgA-HRP antibodies were obtained from Sigma-Aldrich.

In the second case, an ELISA optical detection assay was conducted on 96-well plate, which comprised the following stages:

1) First incubation stage: 70 μL of the 0.2 mg/mL magnetic peptide solution obtained in Example 1 were incubated with 70 μL of the positive and negative controls and test serum on microtritation plates, under shaking conditions for 30 minutes at ambient temperature and then washed three times with 100 μL of PBST, applying a magnetic field between the washes in order to separate the modified MPs of the supernatant.

2) Second incubation stage: 100 μl of anti-human IgA-HRP diluted 1:20,000 were added and the resulting immunocomplex was incubated for 30 minutes at ambient temperature under agitation conditions. Subsequently, the washing stage explained in (1) was newly applied.

3) 100 μL of TMB:$H_2O_2$ (1:1) solution were added to each well and the plate was incubated for 30 minutes in darkness; next, 100 μL of stop solution were added ($H_2SO_4$ 2 M);

4) Lastly, the absorbance of each well was read using a plate reader at λ=450 nm.

With both methods, 23 serums were analysed which had been histologically confirmed by a duodenal biopsy, of which, in turn, 13 and 10 serums were classified as coeliac and non-coeliac, respectively.

Table I shows the results obtained (sensitivity, SE and specificity, ES) with the magnetic peptide of the invention (Example 1) both with the electrochemical immunosensor and ELISA optical immunoassay and the results obtained at the hospitals of origin for the same samples (23) using commercial methods:

TABLE I

| Method | Antibody | SE (%) | ES (%) |
|---|---|---|---|
| m-GEC electrode Electrochemical immunosensor (Invention) | APDG-IgA | 100 | 100 |

TABLE I-continued

| Method | Antibody | SE (%) | ES (%) |
|---|---|---|---|
| ELISA microplate Optical immunoassay (Invention) | APDG-IgA | 100 | 100 |
| Commercial method 1 | AGA-IgA | 96.3 | 50.0 |
| Commercial method 2 | AGA-IgA | 96.2 | 91.7 |
| Commercial method 3 | $ATG_2$-IgA | 95.0 | 99.4 |
| Commercial method 4 | $ATG_2$-IgA | 93.6 | 94.3 |

Table II shows the results obtained (sensitivity, SE, and specificity, ES) with the magnetic peptide of the invention, both with the electrochemical immunosensor and the ELISA optical immunoassay and results disclosed in the state of the art for the detection of anti-PDG antibodies as a diagnosis of coeliac disease:

TABLE II

| Medium | Analytical technique | Iso-type | SE (%) | ES (%) | No. of samples * | Ref. |
|---|---|---|---|---|---|---|
| m-GEC electrode | Electrochemical immunosensor | IgA | 100 | 100 | 23 | Invention |
| ELISA microplate | Optical immunoassay | IgA | 100 | 100 | 23 | Invention |
| Lanthanide solid phase | Immunofluorometric assay | IgA | 92 | 90 | 168 | 1 |
| ELISA microplate | Optical immunoassay | IgA | 97 | 92 | 139 | 2 |
| ELISA microplate | Optical immunoassay | IgA | 85 | 96 | 128 | 3 |

* Positive samples verified by duodenal biopsy
1 Ankelo et al., 2007
2 Sakly et al., 2012
3 Schwertz et al., 2004

It can be observed that the method of the invention presents greater sensitivity and specificity than other methods disclosed in the state of the art based on the detection of antibodies with respect to deaminated gliadin peptides.

Example 3

Assay for the Detection of Coeliac Disease Using Two Types of Magnetic Peptides

The magnetic peptides obtained in Example 1 and in the comparative Example in accordance with a procedure substantially identical to that of Example 2

Eleven Samples Were Analysed: Seven Positive Serums and Four Negative Serums

The results obtained made it possible to conclude that the immunosensor with the magnetic peptide of the invention present, for the different samples, the greatest electrochemical signals and enabled greater differentiation between positive and negative samples with respect to the immunosensor prepared from the peptide obtained in the comparative Example, wherein the peptide was covalently bonded to the magnetic particles modified with the tosyl group.

Table III shows the results obtained:

TABLE III

| Parameter | Example 1 | Comparative example |
|---|---|---|
| Sensitivity (%) | 100 | 86 |
| Specificity (%) | 100 | 75 |
| Efficiency (%) | 100 | 82 |

Examples 4 to 12

Immobilisation of Peptides on Dynabeads®TALON® Magnetic Particles

Other magnetic peptides were prepared in accordance with a procedure substantially identical to the procedure described in Example 1, whose sequences are shown in Table IV below:

TABLE IV

| Example | Peptide | SEQ_ID_NO: |
|---|---|---|
| 4 | $H_2N-(H)_6$-LPFPQQPQQPFPQPQQPQ-COOH | 53 |
| 5 | $H_2N$-LPFPEQPEQPFPQPEQPQ-$(H)_6$-COOH | 54 |
| 6 | $H_2N$-LPFPEQPEQPFPQPEEPQ-$(H)_6$-COOH | 55 |
| 7 | $H_2N$-LPFPEQPEQPFPQPEQPQ-$(H)_2$-COOH | 56 |
| 8 | $H_2N-(H)_4$-LPFPEQPEQPFPQPEQPQ-COOH | 57 |
| 9 | $H_2N-(H)_{10}$-LPFPEQPEQPFPQPEQPQ-COOH | 58 |
| 10 | $H_2N$-LPFPEQPEQPFPQPEQPQ-$(H)_6$-COOH | 59 |
| 11 | $H_2N$-LPFPEQPEQPFPEPEQPQ-$(H)_6$-COOH | 60 |
| 12 | $H_2N-(H)_2$-LPFPEQPEQPFPQPEQPQ-COOH | 61 |

Example 13

Comparative Assay for the Detection of Coeliac Disease Using Magnetic Peptides of a Different Sequence The magnetic peptides obtained in examples 1 and 4 to 12 were comparatively assayed using a coeliac disease positive serum and a negative serum using a procedure substantially identical to that of Example 2. Table V shows the results obtained, expressed as the relationship between the signal of the positive sample and of the negative sample, such as the degree of differentiation between positive and negative samples, wherein a value equal to 1 indicates the non-capacity to discriminate a positive sample from a negative sample and values greater than 1 the capacity to discriminate them:

TABLE V

| Example | SEQ_ID_NO: | Positive signal/ negative signal ratio |
|---|---|---|
| 1 | 39 | 6.5 |
| 4 | 53 | 2.3 |
| 5 | 54 | 7.6 |
| 6 | 55 | 1.9 |
| 7 | 56 | 1.9 |
| 8 | 57 | 2.7 |
| 9 | 58 | 9.8 |
| 10 | 59 | 2.0 |
| 11 | 60 | 1.9 |
| 12 | 61 | 2.5 |

The results obtained made it possible to conclude that the immunosensor with the magnetic peptide of Example 9 presented the greatest differentiation capacity between positive and negative samples, followed by the magnetic peptides of examples 5, 1, 8, 12, 4 and 10.

The invention claimed is:

1. A magnetic peptide characterised in that it comprises:
   a) a peptide of general formula (I):

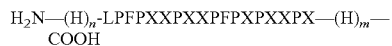

(SEQ ID NO: 62)
   wherein:
   X is equally Q or E and at least one X is E, and
   wherein:
   n is comprised between 2 and 20, and m is 0, or
   m is comprised between 2 and 20, and n is 0, and
   b) a particulated magnetic complex with the general formula (II):

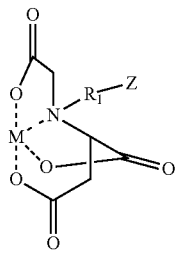

wherein:
   Z is a magnetic polymer particle covalently bonded to the carboxymethylated aspartate ligand through $R_1$,
   $R_1$ is an arm connecting the nitrogen atom of the carboxymethylated aspartate ligand with the magnetic polymer particle Z,
   M is an ion of a transition metal with coordination number 6, and
   connecting arm $R_1$ is selected from -alkylene-NH-alkylene-$R_2$, -alkylene-NH—CO-alkylene-$R_2$, -alkylene-CO—NH-alkylene-$R_2$, -alkylene-O-alkylene-$R_2$, -alkylene-O—CO-alkylene-$R_2$, and -alkylene-CO—O-alkylene-$R_2$, wherein $R_2$ is O, S or NH.

2. The magnetic peptide, according to claim 1, characterised in that the magnetic polymer particle consists of a reticulated styrenic polymer.

3. The magnetic peptide according to claim 1, characterised in that the connecting arm $R_1$ is -alkylene-NH-alkylene-$R_2$, wherein $R_2$ is O, S or NH.

4. The magnetic peptide according to claim 3, characterised in that the connecting arm $R_1$ is —(CH$_2$)$_x$—NH—(CH$_2$)$_y$—NH, wherein x and y are comprised between 1 and 6.

5. The magnetic peptide according to claim 1, characterised in that the transition metal M is selected from the group formed by Ni, Fe, Ga, Mn, Co, Cu and Zn.

6. The magnetic peptide according to claim 5, characterised in that the transition metal M is selected from the group formed by Ni, Fe, Mn and Co.

7. The magnetic peptide according to claim 6, characterised in that the transition metal M is Co.

8. The magnetic peptide, according to claim 7, characterised in that the transition metal has an oxidation state of +2.

9. The magnetic peptide, according to claim 1, characterised in that the particulated magnetic complex is a superparamagnetic polystyrene particle.

10. A kit for detecting coeliac disease, characterised in that it comprises the magnetic peptide of claim 1.

11. An immunosensor, characterised in that it comprises the magnetic peptide of claim 1 and a transducer having a magnet coupled thereto or integrated therewith.

12. A method for detecting coeliac disease, characterised in that it comprises the following stages:
   1) incubating a suspension of the magnetic peptide of claim 1 with a serum or blood sample of an individual,
   2) adding anti-human-HRP, selected from among anti-human IgA-HRP and anti-human IgG-HRP, to the suspension incubated in point 1) and incubate the suspension obtained, and
   3) measuring the electromechanical or optical signal obtained from the suspension obtained in point 2).

* * * * *